US010173055B2

(12) United States Patent
Howard et al.

(10) Patent No.: US 10,173,055 B2
(45) Date of Patent: Jan. 8, 2019

(54) ELECTRICAL STIMULATION LEADS AND SYSTEMS HAVING A RF SHIELD ALONG AT LEAST THE LEAD AND METHODS OF MAKING AND USING

(71) Applicant: Boston Scientific Neuromodulation Corporation, Valencia, CA (US)

(72) Inventors: Joshua Dale Howard, Sacramento, CA (US); Richard Mustakos, Thousand Oaks, CA (US)

(73) Assignee: BOSTON SCIENTIFIC NEUROMODULATION CORPORAATION, Valencia, CA (US)

( * ) Notice: Subject to any disclaimer, the term of this patent is extended or adjusted under 35 U.S.C. 154(b) by 201 days.

(21) Appl. No.: 15/143,297

(22) Filed: Apr. 29, 2016

(65) Prior Publication Data

US 2016/0317805 A1    Nov. 3, 2016

Related U.S. Application Data

(60) Provisional application No. 62/155,304, filed on Apr. 30, 2015.

(51) Int. Cl.
*A61N 1/00* (2006.01)
*A61N 1/08* (2006.01)
(Continued)

(52) U.S. Cl.
CPC .............. *A61N 1/08* (2013.01); *A61N 1/05* (2013.01); *A61N 1/3752* (2013.01);
(Continued)

(58) Field of Classification Search
CPC .................................... A61N 1/08; A61N 1/05
(Continued)

(56) References Cited

U.S. PATENT DOCUMENTS 5,131,388 A    7/1992  Pless et al.
5,336,246 A    8/1994  Dantanarayana
(Continued)

FOREIGN PATENT DOCUMENTS

WO    2010126943    11/2010

OTHER PUBLICATIONS

Partial International Search Report for PCT/US2016/030262 dated Jul. 26, 2016.

(Continued)

*Primary Examiner* — Nadia A Mahmood
(74) *Attorney, Agent, or Firm* — Lowe Graham Jones PLLC; Bruce E. Black

(57) ABSTRACT

An electrical stimulation system includes a lead or lead extension; a control module coupleable to the lead or lead extension; and a continuous conductive RF shield having a first portion extending along at least a portion of the lead and a second portion configured and arranged to form a perimeter band disposed around the housing of the control module. Alternatively, an electrical stimulation lead or lead extension includes a body; first contacts disposed along the distal end portion of the body; second contacts disposed along the proximal end portion of the body; a conductive RF shield disposed over, and extending along, at least a portion of the body; and a non-conductive jacket disposed over the conductive RF shield. The non-conductive jacket defines at least one window which exposes a portion of the conductive RF shield radially beneath the at least one window.

20 Claims, 7 Drawing Sheets

(51) Int. Cl.
*A61N 1/375* (2006.01)
*A61N 1/05* (2006.01)

(52) U.S. Cl.
CPC .......... *A61N 1/0534* (2013.01); *A61N 1/0553* (2013.01); *A61N 1/086* (2017.08)

(58) Field of Classification Search
USPC .................................................. 607/63, 116
See application file for complete search history.

(56) References Cited

U.S. PATENT DOCUMENTS

| | | | |
|---|---|---|---|
| 5,699,801 A | 12/1997 | Atalar et al. |
| 5,825,608 A | 10/1998 | Duva et al. |
| 5,928,145 A | 7/1999 | Ocali et al. |
| 6,031,375 A | 2/2000 | Atalar et al. |
| 6,181,969 B1 | 1/2001 | Gord |
| 6,240,317 B1 | 5/2001 | Villaseca et al. |
| 6,263,229 B1 | 7/2001 | Atalar et al. |
| 6,394,956 B1 | 5/2002 | Chandrasekaran et al. |
| 6,408,202 B1 | 6/2002 | Lima et al. |
| 6,508,765 B2 | 1/2003 | Suorsa et al. |
| 6,510,345 B1 | 1/2003 | Van Bentem |
| 6,516,227 B1 | 2/2003 | Meadows et al. |
| 6,549,800 B1 | 4/2003 | Atalar et al. |
| 6,606,513 B2 | 8/2003 | Lardo et al. |
| 6,609,029 B1 | 8/2003 | Mann et al. |
| 6,609,032 B1 | 8/2003 | Woods et al. |
| 6,628,980 B2 | 9/2003 | Atalar et al. |
| 6,673,999 B1 | 1/2004 | Wang et al. |
| 6,675,033 B1 | 1/2004 | Lardo et al. |
| 6,701,176 B1 | 3/2004 | Halperin et al. |
| 6,714,809 B2 | 3/2004 | Lee et al. |
| 6,741,892 B1 | 5/2004 | Meadows et al. |
| 6,824,515 B2 | 11/2004 | Suorsa et al. |
| 6,898,454 B2 | 5/2005 | Atalar et al. |
| 6,904,307 B2 | 6/2005 | Karmarkar et al. |
| 7,015,393 B2 | 3/2006 | Weiner et al. |
| 7,133,714 B2 | 11/2006 | Karmarkar et al. |
| 7,194,294 B2 | 3/2007 | Panescu et al. |
| 7,236,816 B2 | 6/2007 | Kumar et al. |
| 7,244,150 B1 | 7/2007 | Brase et al. |
| 7,412,276 B2 | 8/2008 | Halperin et al. |
| 7,437,193 B2 | 10/2008 | Parramon et al. |
| 7,551,953 B2 | 6/2009 | Lardo et al. |
| 7,561,906 B2 | 7/2009 | Atalar et al. |
| 7,599,729 B2 | 10/2009 | Atalar et al. |
| 7,620,453 B1 | 11/2009 | Propato et al. |
| 7,672,734 B2 | 3/2010 | Anderson et al. |
| 7,761,165 B1 | 7/2010 | He et al. |
| 7,778,682 B2 | 8/2010 | Kumar et al. |
| 7,822,460 B2 | 10/2010 | Halperin et al. |
| 7,822,484 B1 | 10/2010 | Zhao et al. |
| 7,844,319 B2 | 11/2010 | Susil et al. |
| 17,848,788 | 12/2010 | Tulley et al. |
| 7,949,395 B2 | 5/2011 | Kuzma |
| 7,957,783 B2 | 6/2011 | Atalar et al. |
| 7,974,706 B2 | 7/2011 | Moffitt et al. |
| 8,055,351 B2 | 11/2011 | Atalar et al. |
| 8,108,028 B2 | 1/2012 | Karmarkar |
| 8,175,710 B2 | 5/2012 | He |
| 8,224,450 B2 | 7/2012 | Brase |
| 8,322,026 B2 | 12/2012 | McDonald |
| 8,340,782 B2 | 12/2012 | McDonald et al. |
| 18,335,570 | 12/2012 | McDonald |
| 8,364,278 B2 | 1/2013 | Pianca et al. |
| 8,364,279 B2 | 1/2013 | McDonald et al. |
| 8,380,277 B2 | 2/2013 | Atalar et al. |
| 8,380,324 B2 | 2/2013 | McDonald et al. |
| 8,433,421 B2 | 4/2013 | Atalar et al. |
| 8,478,423 B2 | 7/2013 | McDonald et al. |
| 8,509,876 B2 | 8/2013 | Karmarkar |
| 8,649,842 B2 | 2/2014 | Atalar et al. |
| 8,688,226 B2 | 4/2014 | Atalar et al. |
| 2001/0014820 A1 | 8/2001 | Gielen et al. |
| 2004/0181177 A1 | 9/2004 | Lee et al. |
| 2005/0070972 A1 | 3/2005 | Wahlstrand et al. |
| 2005/0222633 A1 | 10/2005 | Edvardsson |
| 2007/0150036 A1 | 6/2007 | Anderson |
| 2008/0039898 A1 | 2/2008 | Lim et al. |
| 2008/0051854 A1 | 2/2008 | Bulkes et al. |
| 2008/0243218 A1 | 10/2008 | Bottomley et al. |
| 2008/0262584 A1 | 10/2008 | Bottomley et al. |
| 2009/0149906 A1 | 6/2009 | Ameri et al. |
| 2009/0234368 A1 | 9/2009 | Gore |
| 2009/0259272 A1 | 10/2009 | Reddy et al. |
| 2009/0270956 A1 | 10/2009 | Vase et al. |
| 2010/0057175 A1 | 3/2010 | McDonald et al. |
| 2011/0112612 A1 | 5/2011 | Rahman |
| 2011/0137414 A1 | 6/2011 | Litzke et al. |
| 2011/0144449 A1 | 6/2011 | Ortiz et al. |
| 2011/0152999 A1 | 6/2011 | Hastings et al. |
| 2011/0234155 A1 | 9/2011 | Chen et al. |
| 2011/0257703 A1 | 10/2011 | Kerber et al. |
| 2012/0016355 A1 | 1/2012 | George et al. |
| 2012/0035616 A1 | 2/2012 | Olsen et al. |
| 2012/0041528 A1 | 2/2012 | Mehdizadeh et al. |
| 2012/0041529 A1 | 2/2012 | Olsen et al. |
| 2012/0123500 A1 | 5/2012 | Erickson |
| 2012/0158072 A1 | 6/2012 | Venook et al. |
| 2012/0191167 A1 | 7/2012 | McDonald et al. |
| 2012/0221074 A1 | 8/2012 | Brase et al. |
| 2013/0105071 A1 | 5/2013 | DiGiore et al. |
| 2013/0150938 A1 | 6/2013 | Carbunaru et al. |
| 2013/0304170 A1 | 11/2013 | Foster et al. |
| 2014/0034377 A1 | 2/2014 | Vij |
| 2014/0058482 A1* | 2/2014 | Gupta ................ A61N 1/36142 607/63 |
| 2014/0135614 A1 | 5/2014 | Venook et al. |
| 2014/0214130 A1 | 7/2014 | Lopez et al. |
| 2014/0343645 A1 | 11/2014 | Wechter |
| 2015/0031975 A1 | 1/2015 | Atalar et al. |
| 2015/0073506 A1 | 3/2015 | Gupta et al. |
| 2015/0374977 A1 | 12/2015 | Howard et al. |

OTHER PUBLICATIONS

International Search Report and Written Opinion for PCT/US2016/030262 dated Sep. 23, 2016.
Rezai, A. R., et al., "Neurostimulation system used for deep brain stimulation (DBS): MR safety issues and implications of failing to follow guidelines." Investigative Radiology, 39:300-303; 2004.
Nyenhuis, J. A., et al., "MRI and implanted medical devices: basic interactions with an emphasis on heating." IEEE Transactions on Device and Materials Reliability, 5:467-478; 2005.
U.S. Appl. No. 62/139,545, filed Mar. 27, 2015.

* cited by examiner

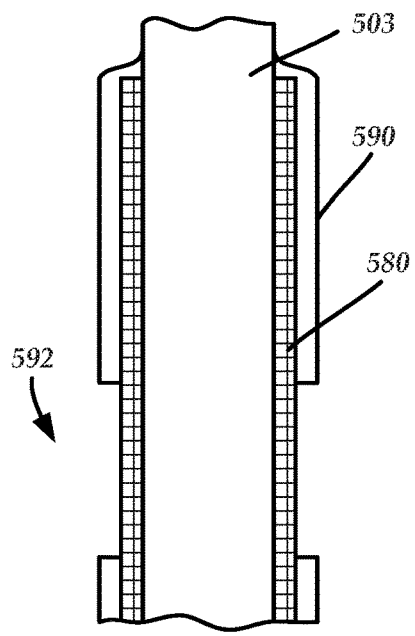
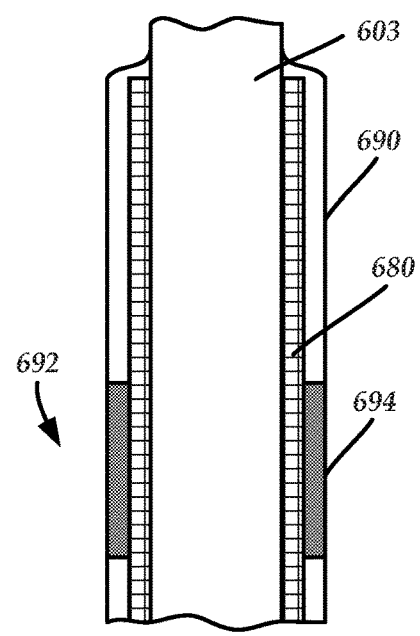
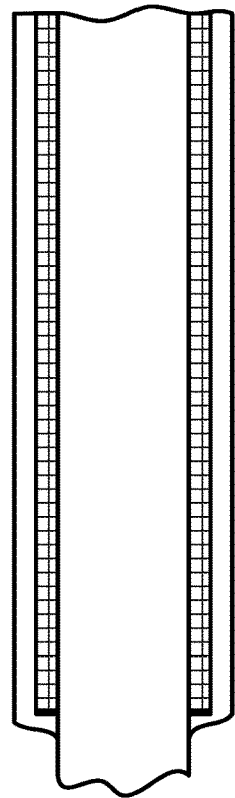
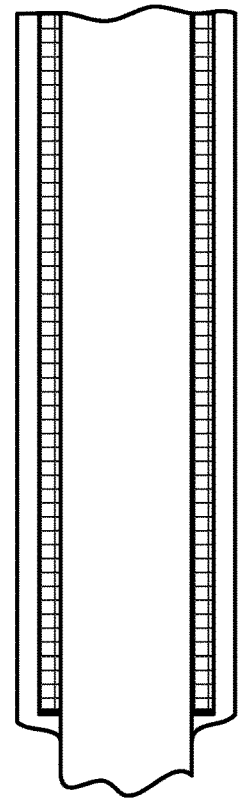
Fig. 5  Fig. 6

ELECTRICAL STIMULATION LEADS AND SYSTEMS HAVING A RF SHIELD ALONG AT LEAST THE LEAD AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/155,304, filed Apr. 30, 2015, which is incorporated herein by reference.

FIELD

The present invention is directed to the area of implantable electrical stimulation systems and methods of making and using the systems. The present invention is also directed to implantable electrical stimulation leads having a RF shield, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an electrical stimulation system that includes a lead having distal end portion, a proximal end portion, and a longitudinal length and including electrodes disposed along the distal end portion of the lead, terminals disposed along the proximal end portion of the lead, and conductors coupling the terminals to the electrodes; a control module coupleable to the lead and including a housing and an electronic subassembly disposed in the housing; and a continuous conductive RF shield including a first portion extending along at least a portion of the lead and a second portion configured and arranged to form a perimeter band disposed around the housing of the control module. In at least some embodiments, the first portion of the RF shield forms a tubular structure disposed around the portion of the lead.

Another embodiment is an electrical stimulation system that includes a lead having distal end portion, a proximal end portion, and a longitudinal length and including electrodes disposed along the distal end portion of the lead, terminals disposed along the proximal end portion of the lead, and conductors coupling the terminals to the electrodes; a lead extension coupleable to the lead and having distal end portion, a proximal end portion, and a longitudinal length and including a connector disposed along the distal end portion of the lead extension and configured and arranged to receive the proximal end portion of the lead, contacts disposed within the connector, terminals disposed along the proximal end portion of the lead extension, and conductors coupling the terminals to the contacts; a control module coupleable to the lead extension and including a housing and an electronic subassembly disposed in the housing; and a continuous conductive RF shield including a first portion extending along at least a portion of the lead extension and a second portion configured and arranged to form a perimeter band disposed around the housing of the control module. In at least some embodiments, the first portion of the RF shield forms a tubular structure disposed around the portion of the lead extension.

In at least some embodiments of any of the systems described above, the second portion forms the perimeter band that attaches at both ends to the first section. In at least some embodiments of any of the systems described above, the second portion forms the perimeter band that is attached at one end to the first section and is configured and arranged to terminate at a position along a perimeter of the control module. In at least some embodiments of any of the systems described above, the housing of the control module includes a conductive portion with the RF shield conductively coupled to the conductive portion of the housing. In at least some embodiments of any of the systems described above, the control module is coupled to the lead or the lead extension and the RF shield forms the perimeter band. In at least some embodiments of any of the systems described above, the lead includes a non-conductive jacket and at least part of the first portion of the RF shield is disposed radially beneath the non-conductive jacket.

A further embodiment is an electrical stimulation lead or lead extension that includes a body having a distal end portion, a proximal end portion, a longitudinal length, and a circumference; first contacts disposed along the distal end portion of the body; second contacts disposed along the proximal end portion of the body; conductors electrically coupling the first contacts to the second contacts; a conductive RF shield disposed over, and extending along, at least a portion of the body that is distal to the second contacts and proximal to the first contacts; and a non-conductive jacket disposed over the conductive RF shield and having a circumference. The non-conductive jacket defines at least one window which exposes a portion of the conductive RF shield radially beneath the at least one window.

In at least some embodiments, the non-conductive jacket is part of the lead body. In at least some embodiments, the at least one window is multiple windows. In at least some embodiments, each of the at least one window extends entirely around the circumference of the jacket. In at least some embodiments, the electrical stimulation lead or lead extension further includes at least one conductive contact with each conductive contact disposed in a one of the at least one window and conductively attached to the conductive RF shield.

Yet another embodiment is an electrical stimulation system that includes any one of the electrical stimulation lead or lead extension describe above; a control module coupleable to the electrical stimulation lead or lead extension and including a housing, an electronic subassembly disposed in the housing; and a connector for receiving the proximal end portion of the electrical stimulation lead or lead extension. The connector has a proximal end, a distal end, and a longitudinal length and includes a connector housing defining a port at the distal end of the connector for receiving the proximal end portion of the body of the electrical stimulation lead or lead extension, and connector contacts disposed in the connector housing to couple to at least one of the second contacts disposed on the proximal end portion of the body of the electrical stimulation lead or lead extension.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5 is a schematic longitudinal partial cross-sectional view of one portion of a lead with a conductive RF shield and non-conductive jacket defining a window, according to the invention;

FIG. 6 is a schematic longitudinal partial cross-sectional view of one portion of a lead with a conductive RF shield, non-conductive jacket defining a window, and a conductive contact disposed in the window, according to the invention.

DETAILED DESCRIPTION

The present invention is directed to the area of implantable electrical stimulation systems and methods of making and using the systems. The present invention is also directed to implantable electrical stimulation leads having a RF shield, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
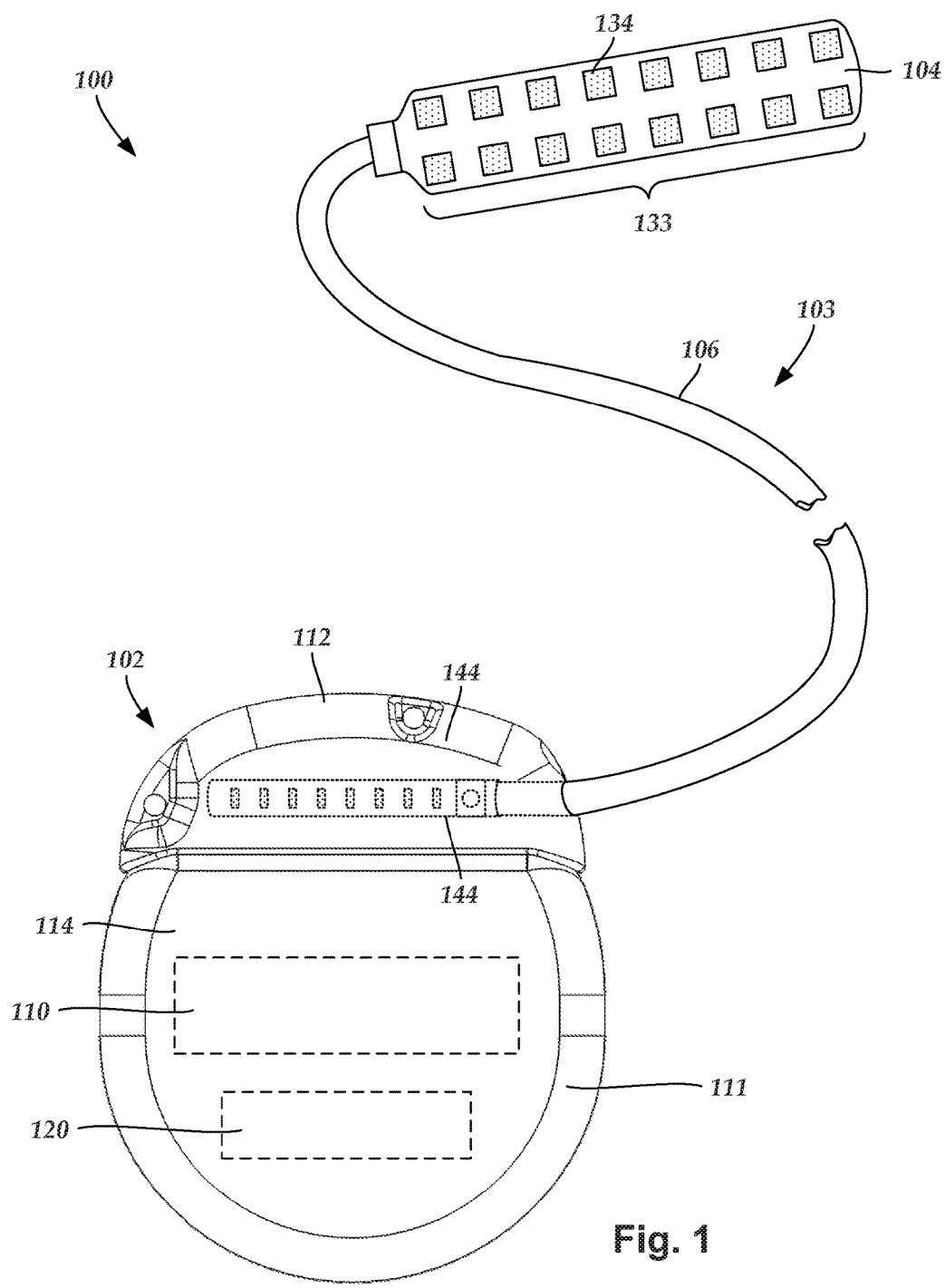
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having one lead body 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
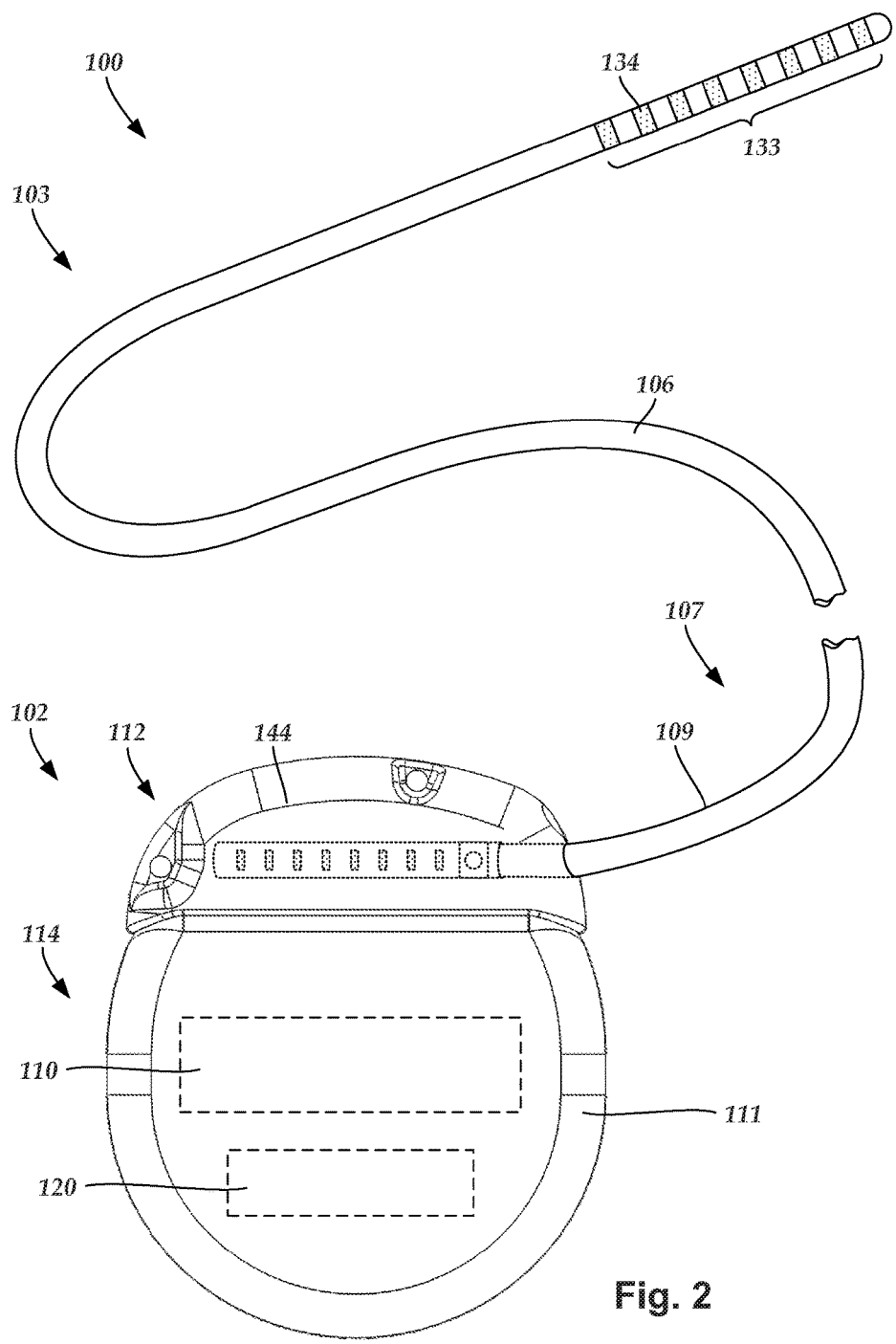
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

With reference to FIGS. 1 and 2, the control module 102 typically includes a housing 111 that can be subdivided into, for example, a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
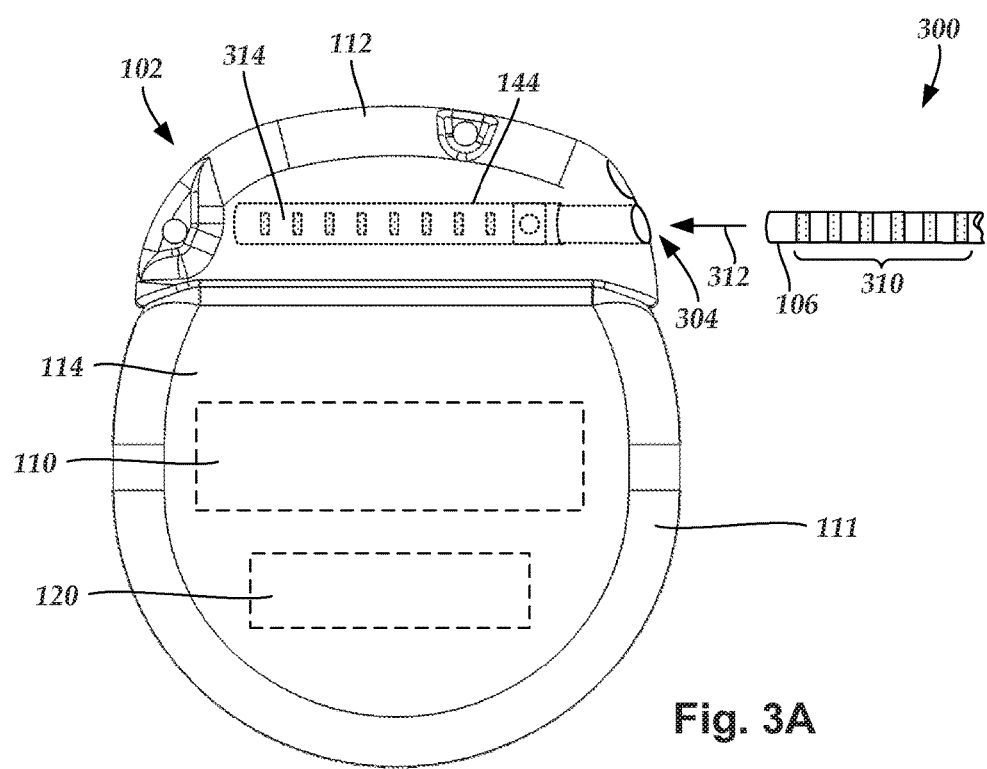
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrow 312. In FIG. 3A (and in other figures), the connector housing 112 is shown having one port 304. The connector housing 112 can define any suitable number of ports including, for example, one, two, three, four, five, six, seven, eight, or more ports.

The control module connector 144 also includes a plurality of connector contacts, such as connector contact 314, disposed within each port 304. When the elongated device 300 is inserted into the port 304, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
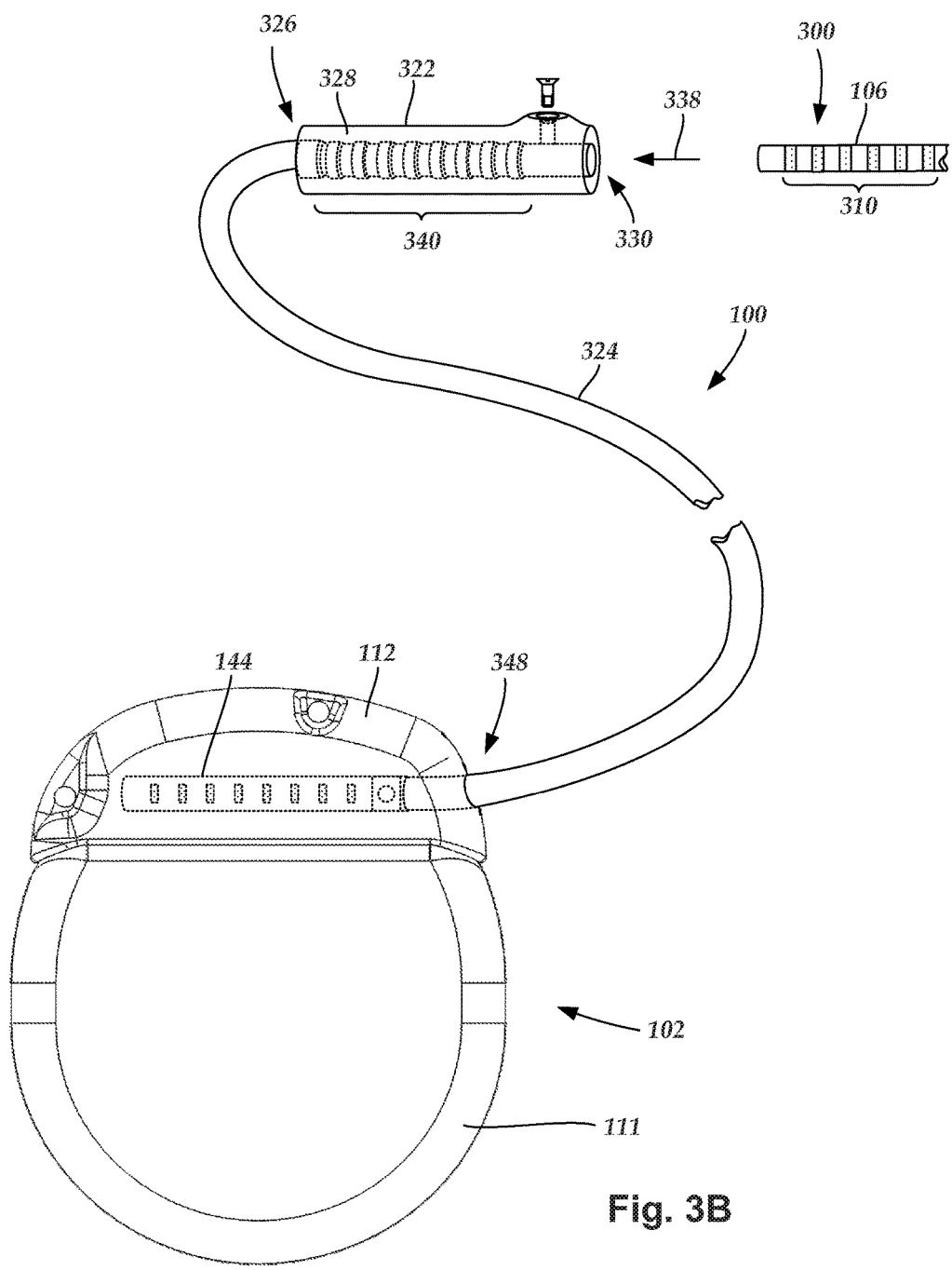
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Conventional electrical stimulation systems may be potentially unsafe for use when exposed to RF irradiation, such as during a magnetic resonance imaging ("MRI") procedure. A common cause of the electrical interaction between the electrical stimulation system and RF irradiation is common-mode coupling of the applied electromagnetic field. The interaction can be modeled as a series of distributed sources along the elongated conductive structures of the electrical stimulation system, such as leads, or conductors within leads. Common-mode induced RF currents may reach amplitudes of greater than one ampere in MRI environments. Such currents can cause heating and potentially disruptive voltages within electronic circuits.

A RF shield can be used to reduce or eliminate the inducement of current in the conductors of the lead. Current will be induced in the RF shield, however, and can be dissipated in a safe manner.

Figure 4A:
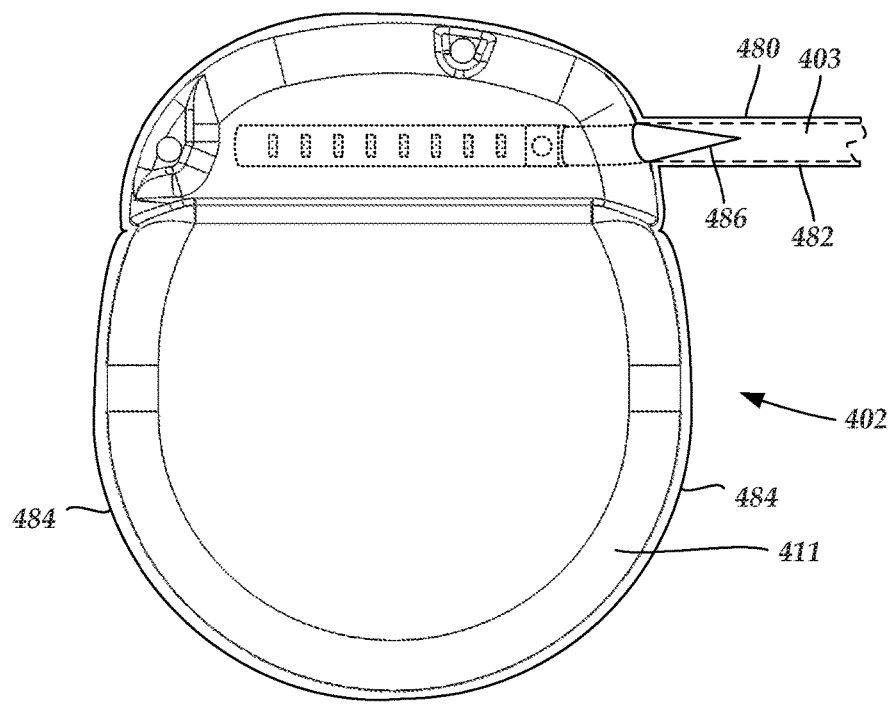
FIG. 4A is a schematic side view of one embodiment of a control module and a portion of a lead with a continuous conductive RF shield disposed on a portion of the lead and forming a perimeter band around the control module, according to the invention.
Figure 4B:
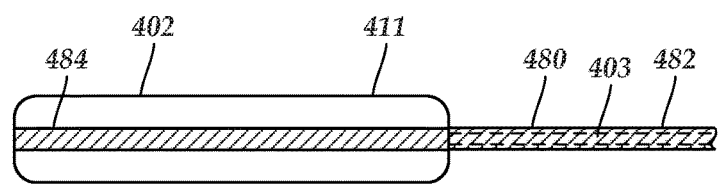
FIG. 4B is a schematic top view of the control module and portion of the lead of FIG. 4A, according to the invention.

FIG. 4A is a side view and FIG. 4B is a top view illustrating one embodiment of a system that incorporates an RF shield 480 with a lead 403 and control module 402. The RF shield 480 has a first portion 482 disposed along at least a portion of the lead 403 and a second portion 484 that forms a perimeter band around the housing 411 of the control module 402.

The RF shield 480 is made of a conductive material, such as a metal or alloy. The RF shield 480 can have any suitable form including, but not limited, a solid structure, a braided structure, a coiled structure, a mesh, one or more strips or the like, a set of cross-linked strips, or the like or any combination thereof.

In at least some embodiments, the first portion 482 of the RF shield 480 is tubular and fits over a portion of the lead, although other arrangements, such as one or more strips extending along the exterior of the lead or a tube or strip(s) disposed within a jacket of the lead and exiting the lead to form the perimeter band, can also be used. In at least some embodiments, the RF shield 480 terminates proximal to the electrodes 134 (FIGS. 1 and 2) of the lead. In at least some embodiments, particularly for use in deep brain stimulation, the RF shield 480 terminates proximal to a portion of the lead that is to be inserted into the cranium or brain of the patient. It will be understood, however, that the RF shield can terminate at any other suitable position along the length of the lead.

The second portion 484 extends from the first portion 482 and is disposed around at least a portion of the perimeter of the control module 402. In at least some embodiments, such as the illustrated embodiment of FIGS. 4A and 4B, the second portion 484 extends completely around the control module 402 and both ends of the second portion 484 terminate at the first portion 482. In other embodiments, the second portion 484 can terminal elsewhere, for example, at any position along the perimeter of the control module 402. In at least some embodiments, such as the illustrated embodiment of FIGS. 4A and 4B, the RF shield 480 splits at a junction 486 between the first portion 482 and the second portion 484 so that the second portion 484 can form a loop the encompasses the control module 402.

The second portion 484 is preferably electrically coupled to the conductive housing 411 of the control module 402 so that the control module can ground the RF shield 480. Alternatively or additionally, the RF shield 480 can dissipate current into tissue near the first portion 482 or second portion 484 or both. Because the RF shield 480 has much more surface area than the electrodes 134, the current density of the dissipating current will be much less than it would if the induced current were dissipated into tissue by the electrodes. This arrangement, therefore, reduces or eliminates the likelihood of causing tissue damage due to heating arising from the dissipation of induced current. In addition, the RF shield can be positioned so that induced current is dissipated into less sensitive tissue. For example, in deep brain stimulation, the RF shield can be positioned so that it is not in contact with sensitive brain tissue and, therefore, any dissipation of current from the RF shield can occur in other portions of the body.

In at least some embodiments, the second portion 484 can be disposed around the control module 402 during the implantation procedure for the lead 403 and control module. In other embodiments, the lead 403 and control module 402 can be pre-assembled with the second portion 484 disposed around the perimeter of the control module. In at least some embodiments, an existing lead can be retrofitted to include the RF shield 480 by sliding the RF shield onto the lead.

The embodiment illustrated in FIGS. 4A-4B is described with respect to a lead. It will be recognized that the RF shield can also be implemented, as described, except with a lead extension instead of the lead.

The embodiment illustrated in FIGS. 4A-4B is described with respect to a single lead. It will be understood, however, that multiple leads/lead extensions, or multiple proximal end portions of a single lead/lead extension (or any combination thereof), can be inserted into a control module with multiple ports. (See, for example, U.S. Patent Application Publication No. 2014/0343645, incorporated herein by reference.) Two or more (or each) of these leads, lead extensions, or proximal end portions can have a RF shield associated with it and each RF shield can have a second portion disposed around the control module, as described above. In some embodiments, two or more of the second portions of the RF shields can be attached together or otherwise in conductive contact. In some embodiments, two or more of the second portions of the RF shields can be isolated from each other.

FIG. 5 illustrates another embodiment of a portion of a lead 503 that includes a RF shield 580 and a jacket 590. The RF shield 580 is disposed on the lead in a region between, but not including, the terminals and the electrodes. In at least some embodiments, particularly for use in deep brain stimulation, the RF shield 580 terminates proximal to a portion of the lead that is to be inserted into the cranium or brain of the patient. It will be understood, however, that the RF shield can terminate at any other suitable position along the length of the lead.

The RF shield 580 is made of a conductive material, such as a metal or alloy. The RF shield 580 can have any suitable form including, but not limited, a solid structure, a braided structure, a coiled structure, a mesh, a set of cross-linked strips, or the like or any combination thereof. The RF shield 580 can be a tube, one or more strips extending along the lead, or any other suitable arrangement.

The jacket 590 is made of a non-conductive material, such as, for example, silicone or polyurethane or any other suitable biocompatible material. In the embodiment of FIG. 5, the jacket 590 is illustrated as being disposed over a portion of the lead 503. Such an arrangement is particularly useful if an existing lead is retrofitted to include the RF shield and jacket. In other embodiments, the jacket is part of the lead body and the RF shield is embedded within the lead body. In the illustrated embodiment of FIG. 5, both ends of the RF shield 580 are covered by the jacket 590. In other embodiments, one or both ends of the RF shield are exposed outside the jacket.

Along the length of the jacket 590, there are one or more windows 592. The windows 592 expose the RF shield 580 so that the RF shield is in contact with patient tissue when the lead 503 is implanted. This arrangement allows the RF shield 580 to dissipate induced current to the tissue surrounding the window. This can reduce or prevent unwanted current from being dissipated into the control module or from being dissipated at the electrodes causing unwanted electrical stimulation or tissue heating. In addition, the windows can be positioned so that induced current is dissipated into less sensitive tissue. For example, in deep brain stimulation, the windows can be positioned so that they are not in contact with sensitive brain tissue and, therefore, any dissipation of current from the RF shield can occur in other portions of the body.

There can be any number of windows 592 along the jacket 590 including one, two, three, four, five, six, eight, ten, twelve, or more windows. When there are more than two windows 592, the windows can be unformly or non-uniformly spaced apart.

Each window 592 can extend around the full circumference of the lead 502, as illustrated in FIG. 5, or extend only partially (for example, no more than 90%, 80%, 75%. 50%, 34%, 25%, or less) around the circumference of the lead. The size and shape of the windows 592 can be the same or different.

The embodiment illustrated in FIG. 5 is described with respect to a lead. It will be recognized that the RF shield can also be implemented, as described, except with a lead extension instead of the lead. Additionally, an RF shield as described can also be implemented on the lead that is attached to the lead extension.

FIG. 6 illustrates another embodiment of a lead 603 that includes a RF shield 680 and a jacket 690. This embodiment is similar to that of FIG. 5 except that a conductive contact 694 is disposed in one or more (or even all) of the windows 692. The design considerations and arrangement of the elements of the embodiment of FIG. 6 is the same as like-named elements of the embodiment of FIG. 5 except as indicated below.

Each conductive contact 694 is electrically coupled to the RF shield 680 to allow for dissipation of current through the conductive contact. The windows and conductive contacts can be positioned so that induced current is dissipated into less sensitive tissue. For example, in deep brain stimulation, the windows and conductive contacts can be positioned so that they are not in contact with sensitive brain tissue and, therefore, any dissipation of current from the RF shield can occur in other portions of the body.

In at least some embodiments, the conductive contacts 694 have an outer diameter that is equal to, or larger than, the outer diameter of the jacket 690. The presence of the conductive contacts 694 can reduce or eliminate the in-growth of tissue between the RF shield 680 and the jacket 690.

The embodiment illustrated in FIG. 6 is described with respect to a lead. It will be recognized that the RF shield can also be implemented, as described, except with a lead extension instead of the lead. Additionally, an RF shield as described can also be implemented on the lead that is attached to the lead extension.

In some embodiments, a lead and a lead extension can both include RF shields 580, 680 and the RF shields can be electrically coupled together. For example, the RF shields may extend over a connector, splitter, or adapter to make a connection. (See, for example, U.S. Provisional Patent Application Ser. No. 62/018,295, incorporated herein by reference.) In addition, in some embodiments, a lead or lead extension can include an RF shield 580, 680, as illustrated in FIG. 5 or 6, and a lead extension can include an RF shield 480 as illustrated in FIG. 4. Optionally, these two RF shield can be conductively coupled to each other.

It will also be understood that there may be multiple lead extensions in any of the embodiments described herein and that each lead extension can include one of the RF shields described herein.

Figure 7:
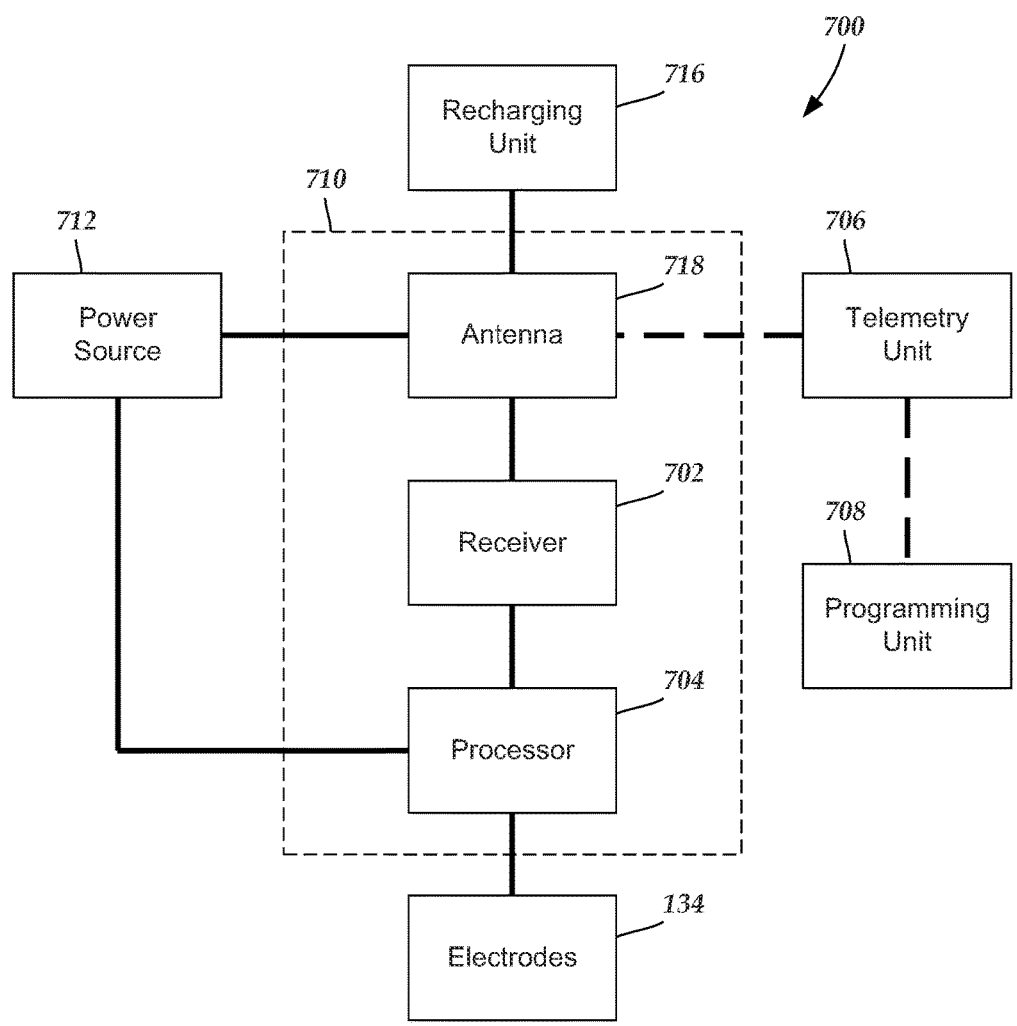
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, a power source 712, an antenna 718, a receiver 702, and a processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 selects which electrode(s) are cathodes and which electrode(s) are anodes. In some embodiments, the processor 704 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by the programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and the receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include the antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An electrical stimulation system, comprising:
   a lead having distal end portion, a proximal end portion, and a longitudinal length, the lead comprising a plurality of electrodes disposed along the distal end portion of the lead, a plurality of terminals disposed along the proximal end portion of the lead, and a plurality of conductors coupling the plurality of terminals to the plurality of electrodes;
   a control module coupleable to the lead and comprising a housing and an electronic subassembly disposed in the housing, wherein the control module comprises a port configured to receive the proximal end portion of the lead; and
   a continuous conductive RF shield comprising a first portion extending along a portion of the lead and a second portion configured and arranged to form a perimeter band disposed around the housing of the control module, wherein, when the end portion of the lead is received in the port of the control module, the first portion or the continuous conductive RF shield extends away from the control module along the portion of the lead.

2. The electrical stimulation system of claim 1, wherein the first portion forms a tubular structure disposed around the portion of the lead.

3. The electrical stimulation system of claim 1, wherein the second portion forms the perimeter band that attaches at both ends to the first portion.

4. The electrical stimulation system of claim 1, wherein the second portion forms the perimeter band that is attached at one end to the first portion and is configured and arranged to terminate at a position along a perimeter of the control module.

5. The electrical stimulation system of claim 1, wherein the housing of the control module comprises a conductive portion, wherein the continuous conductive RF shield is conductively coupled to the conductive portion of the housing.

6. The electrical stimulation system of claim 1, wherein the control module is coupled to the lead and the continuous conductive RF shield forms the perimeter band.

7. The electrical stimulation system of claim 1, wherein the lead comprises a non-conductive jacket and at least part of the first portion of the continuous conductive RF shield is disposed radially beneath the non-conductive jacket.

8. The electrical stimulation system of claim 7, wherein the non-conductive jacket defines at least one window which exposes a portion of the continuous conductive RF shield radially beneath the at least one window.

9. The electrical stimulation system of claim 8, wherein the at least one window is a plurality of windows.

10. The electrical stimulation system of claim 7, wherein each of the at least one window extends entirely around a circumference of the non-conductive jacket.

11. The electrical stimulation system of claim 7, further comprising at least one conductive contact, wherein each conductive contact is disposed in a one of the at least one window and is conductively attached to the continuous conductive RF shield.

12. The electrical stimulation system of claim 7, wherein the lead comprises a lead body and the non-conductive jacket is part of the lead body.

13. The electrical stimulation system of claim 1, wherein the continuous conductive RF shield comprises a braided structure or a set of cross-linked strips.

14. The electrical stimulation system of claim 1, wherein the continuous conductive RF shield comprises a coiled structure.

15. The electrical stimulation system of claim 1, wherein the continuous conductive RF shield comprises a mesh.

16. The electrical stimulation system of claim 1, wherein the continuous conductive RF shield terminates proximal to the electrodes.

17. The electrical stimulation system of claim 1, wherein the lead is configured for deep brain stimulation and the continuous conductive RF shield terminates proximal to a portion of the lead configured for implantation in a cranium or brain.

18. The electrical stimulation system of claim 1, wherein the proximal end portion of the lead is disposed within the port of the control module and the second portion of the continuous conductive RF shield is disposed around the housing of the control module.

19. The electrical stimulation system of claim 18, wherein the second portion forms the perimeter band that is attached at one end to the first portion and terminates at a position along a perimeter of the control module.

20. The electrical stimulation system of claim 18, wherein the second portion forms the perimeter band that attaches at both ends to the first portion and is looped around the control module.

* * * * *